(12) United States Patent
Tanimoto et al.

(10) Patent No.: US 7,897,813 B2
(45) Date of Patent: Mar. 1, 2011

(54) REACTOR FOR GAS PHASE CATALYTIC OXIDATION AND A PROCESS FOR PRODUCING ACRYLIC ACID USING IT

(75) Inventors: Michio Tanimoto, Himeji (JP); Daisuke Nakamura, Yokohama (JP); Nobuyuki Hakozaki, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 610 days.

(21) Appl. No.: 11/826,630

(22) Filed: Jul. 17, 2007

(65) Prior Publication Data
US 2008/0021242 A1   Jan. 24, 2008

(30) Foreign Application Priority Data
Jul. 19, 2006   (JP) .................. 2006-197462

(51) Int. Cl.
*C07C 51/16*   (2006.01)
(52) U.S. Cl. ........................ 562/545; 562/547
(58) Field of Classification Search .............. 562/545, 562/547; 422/201
See application file for complete search history.

(56) References Cited

U.S. PATENT DOCUMENTS

| | | | |
|---|---|---|---|
| 2,532,756 A | 12/1950 | Brunjes et al. | |
| 4,203,906 A | 5/1980 | Takada et al. | |
| 4,256,783 A | 3/1981 | Takada et al. | |
| 4,365,087 A | 12/1982 | Kadowaki et al. | |
| 5,048,601 A | 9/1991 | Yamaguchi et al. | |
| 5,110,564 A | 5/1992 | Herbort | |
| 6,069,271 A | 5/2000 | Tanimoto et al. | |
| 6,808,689 B1 | 10/2004 | Matsumoto et al. | |
| 2004/0115119 A1* | 6/2004 | Olbert et al. | 423/502 |
| 2004/0254402 A1* | 12/2004 | Sioli | 568/472 |
| 2006/0135813 A1* | 6/2006 | Dieterle et al. | 562/546 |

FOREIGN PATENT DOCUMENTS

| | | |
|---|---|---|
| EP | 1 097 745 | 5/2001 |
| EP | 1 166 864 | 1/2002 |
| EP | 1 350 566 | 10/2003 |
| JP | 53-15314 | 2/1978 |
| JP | 54-19479 | 2/1979 |
| JP | 54-21966 | 2/1979 |
| JP | 55-102536 | 8/1980 |
| JP | 7-73674 | 8/1995 |
| JP | 11-130722 | 5/1999 |
| JP | 2001-137689 | 5/2001 |
| WO | 2004/052777 | 6/2004 |

\* cited by examiner

*Primary Examiner* — Taylor Victor Oh
(74) *Attorney, Agent, or Firm* — Wenderoth, Lind & Ponack, L.L.P.

(57) ABSTRACT

Conventional gas-phase catalytic oxidation reaction apparatus comprising two reactors for production of acrylic acid is subject to problems of high equipment costs for the reactors and piping, necessity for wide installation area and easy accumulation of carbides generated by autoxidation of acrolein. On the other hand, conventional reaction apparatus comprising a single reactor has the drawbacks that the composition of gas in the first stage reaction and in the second stage reaction cannot be optimized independently of each other, and that the allowable concentration of starting propylene is limited because of the risk of explosion. As a reaction apparatus to solve these problems, this invention provides a fixed bed shell-and-tube reaction apparatus comprising a single reactor, characterized in that the inside of the reactor is divided into two reaction zones of the first reaction zone and the second reaction zone, and that a space equipped with a mechanism for introducing a gaseous substance from outside is provided between the two reaction zones.

9 Claims, 6 Drawing Sheets

REACTOR FOR GAS PHASE CATALYTIC OXIDATION AND A PROCESS FOR PRODUCING ACRYLIC ACID USING IT

TECHNICAL FIELD

This invention relates to a fixed bed shell-and-tube heat-exchanger type reactor for operating gas-phase catalytic oxidation. More specifically, the invention relates to a fixed bed shell-and-tube heat exchanger type reactor which is used for efficiently producing acrylic acid by gas-phase catalytic oxidation of propylene with a single reactor.

BACKGROUND ART

Production of acrylic acid by two-stage gas-phase catalytic oxidation of propylene has been widely practiced on industrial scale. This reaction consists of the first stage reaction for gas-phase catalytic oxidation of propylene to acrolein and the second stage reaction for gas-phase catalytic oxidation of the acrolein to acrylic acid.

Heretofore proposed methods for practicing the reaction can be broadly classified into two, i.e., those using two reactors and those using a single reactor.

As one of the methods using two reactors, for example, JP Sho 53(1978)-15314A and JP Sho 55(1980)-102536A (corres. to U.S. Pat. No. 4,365,087) disclose a method using two reactors of the first stage reactor filled with a first stage catalyst suitable for the first stage reaction and the second stage reactor filled with a second stage catalyst suitable for the second stage reaction, and comprising introducing the reaction gas containing mainly acrolein as discharged from the first stage reactor, together with recycle gas, oxygen, or inert gas such as nitrogen or steam into the second stage reactor, and further oxidizing the acrolein to produce acrylic acid.

On the other hand, as one of the methods for producing acrylic acid from propylene using a single reactor, for example, JP Sho 54(1979)-19479A (corres. to U.S. Pat. No. 4,203,906), JP Sho 54(1979)-21966A (corres. to U.S. Pat. No. 4,203,906) and JP Hei 11(1999)-130722A (corres. to U.S. Pat. No. 6,069,271) disclose a method for producing acrylic acid from propylene using a single reactor whose shell space is divided into two reaction zones with a partition plate, which is so designed that a heat transfer medium can be circulated at the shell space of each of the reaction zones independently of each other, the reaction tubes in one of the reaction zones being filled with a first stage catalyst suitable for the first stage reaction and the reaction tubes in the other reaction zone being filled with a second stage catalyst suitable for the second stage reaction.

JP 2001-137689A (corres. to U.S. Pat. No. 6,808,689) discloses a technique to enhance the elimination efficiency of the heat generated in the oxidation reaction by a heat transfer medium, by means of baffle plates or the like which are mounted inside of each shell to regulate the flow of the heating medium.

Also JP Hei 7(1995)-73674B (corres. U.S. Pat. No. 5,048,601) discloses a technique of fixing a partition plate or plates on inner wall of the shell, through a cylindrical fixing plate.

Problems to be Solved by the Invention

When two reactors are used as above-described, however, large costs for installation of the reactors, pipe arrangement and the like are incurred, floor area for their installation must also be large, and large scale equipments are required. Furthermore, because the residence time of the gas in the piping up to the introduction of the gas containing mainly acrolein from the first stage reactor into the second stage reactor is relatively long, autoxidation of the acrolein is apt to take place and carbides or the like accompanying the autoxidation are apt to accumulate in the pipe. Still in addition, such carbides and the like pollute the catalyst, which induces such phenomena as deterioration in catalytic performance, blocking of the reaction tubes and pressure loss, within a relatively short period.

Whereas, when a single reactor is used as above-described, it is necessary to have the starting gas in the first stage reaction contain oxygen in advance, in an amount sufficient for its consumption at both the first stage reaction and the second stage reaction. Hence the composition of the gases for the first stage reaction and the second stage reaction cannot be optimized independently of each other. Besides, even when it is desired to raise the starting propylene concentration to improve productivity, since the oxygen of the amount necessary for the second stage reaction must be contained in the starting gas in the first stage reaction, the first stage reaction is carried out in the presence of excessive amount of oxygen, which substantially affects performance of the catalysts. There is still another problem of the limitation on raising propylene concentration, incurred by explosion risk.

Thus, the object of the present invention is to solve such problems in conventional technique for fixed bed shell-and-tube reactors using a single reactor, i.e., to provide a new reactor which enables variation in the gaseous composition in the second stage reaction, in the production process of acrylic acid from propylene.

Means for Solving the Problems

We have discovered that the above object could be accomplished by the use of a fixed bed shell-and-tube reaction apparatus comprising a single reactor for production of acrylic acid by catalytic oxidation reaction of propylene, which is characterized in that the inside of the reactor is divided into two reaction zones of the first reaction zone and the second reaction zone and that a space equipped with a mechanism for introducing a gaseous substance from outside is provided between the two reaction zones, and completed the present invention.

The reactor which is the object to be improved by the present invention has the construction that plural reaction tubes are accommodated in a shell which is demarcated by two upper and lower plates, the reaction tubes are filled with catalysts into which a starting gas for the reaction is fed to be subjected to gas-phase catalytic oxidation, and a heat transfer medium is circulated through the shell space to whereby eliminate the heat of reaction.

More specifically, the present invention concerns a fixed bed shell-and-tube reaction apparatus composed of a single reactor for producing acrylic acid by gas-phase catalytic oxidation, which is characterized by the following construction:

(1) inside of the reactor is divided into two reaction zones of the first reaction zone and the second reaction zone, and between the two reaction zones a space equipped with a mechanism for introducing a gaseous substance from outside is provided;

(2) preferably a mechanism for mixing the outlet gas from the first reaction zone with an additional gas from outside is provided in said space;

(3) preferably said space is filled with a substance which is substantially inert to the reaction gas; and (4) preferably a gas temperature control section for adjusting the reaction gas temperature is provided at the inlet portion of the second reaction zone.

Effect of the Invention

According to the present invention, a new reaction apparatus for producing acrylic acid from propylene is provided, which, because of the adoption of above-described construction, is free from the problems inherent in conventional fixed bed shell-and-tube reaction apparatus using a single reactor, enables change in composition of the gas in the second stage reaction and allows use of propylene at high concentration.

The present invention also provides a production method of acrylic acid using the above reaction apparatus, in which accumulation of carbides is rendered difficult even during a long term operation and in consequence the acrylic acid production is conducted at higher efficiency.

BRIEF EXPLANATION OF DRAWINGS

In FIGS. 1-6, 1 is a reaction tube, 2 is an upper tube plate, 3 is a middle tube plate, 4 is a lower tube plate, 5 is a heat transfer medium-dispersing plate (buffle plate), 6 is an inert substance filled in the space, 7 is an inert substance filled in the gas temperature control section, and 8 denotes blowoff openings for the gas.

BEST EMBODIMENT FOR PRACTICING THE INVENTION

Figure 3:
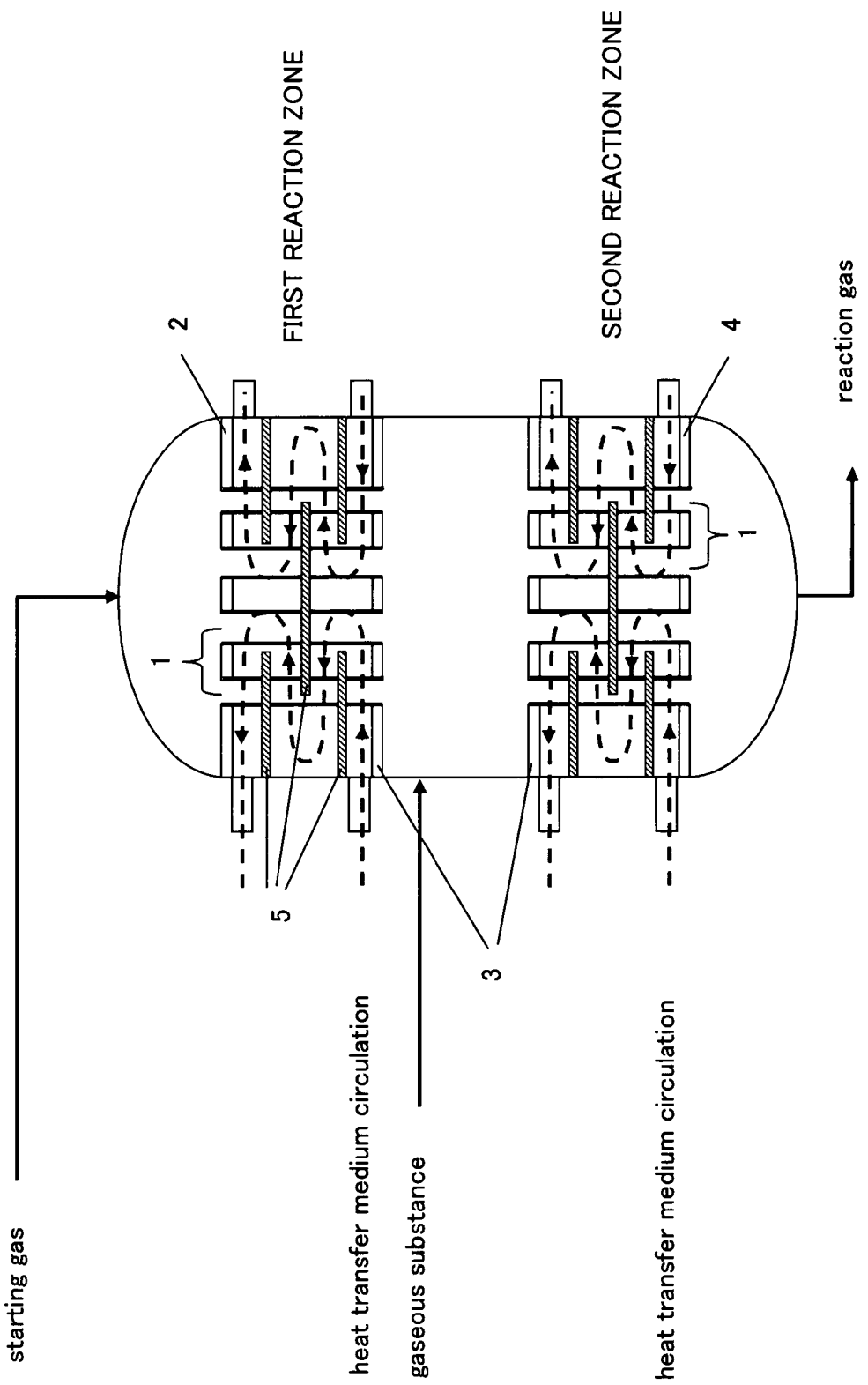
FIG. 3 is a schematic diagram of a reaction apparatus according to the present invention. In the illustrated embodiment, the starting gas is introduced from the top part of the reactor, and a space equipped with a mechanism for introducing a gaseous substance from outside is provided between the two reaction zones.

FIG. 3 shows an embodiment of the reactor according to the present invention. Production of acrylic acid by gas-phase catalytic oxidation of propylene using the reactor of FIG. 3 is explained hereinbelow.

In FIG. 3, the starting gas for the reaction is fed from above the reactor, but the flowing direction of the starting gas is not particularly limited, but can be suitably selected depending on the circumstances.

When the starting gas is supplied from above the reactor, there are provided inside the reactor, from the top to bottom, the first reaction zone, the space and the second reaction zone. Reaction tubes in the first reaction zone are filled with a suitable catalyst to convert propylene into acrolein (which catalyst may be hereafter referred to as the first stage catalyst), the space is equipped with a mechanism for introducing a gaseous substance from outside the reactor, and the reaction tubes in the second reaction zone are filled with a suitable catalyst to convert acrolein into acrylic acid (hereafter may be referred to as the second stage catalyst). A starting gas containing propylene and molecular oxygen is supplied from the top of the reactor into the first reaction zone and converted to acrolein there. The reaction gas which left the first reaction zone flows into the space where it is mixed with an additional gas (e.g., recycled gas, air or the like) separately supplied from outside and flows into the second reaction zone, converted to acrylic acid there and flows out of the reactor.

As the first stage catalyst, any oxidation catalyst customarily used for producing acrolein by gas-phase oxidation of starting gas containing propylene can be used. Similarly, the second stage catalyst is subject to no particular limitation and any oxidation catalyst customarily used for production of acrylic acid by gas-phase oxidation of the reaction gas containing mainly acrolein, which is obtained from the first stage reaction in two-stage gas-phase catalytic oxidation process can be used.

As specific examples of the first stage catalyst, oxide catalysts represented by the following general formula (I):

$$Mo_a Bi_b Fe_c X1_d X2_e X3_f X4_g O_x \quad (I)$$

(wherein Mo is molybdenum; Bi is bismuth; Fe is iron; X1 is at least one element selected from cobalt and nickel; X2 is at least one element selected from alkali metals, alkaline earth metals and thallium; X3 is at least one element selected from tungsten, silicon, aluminum, zirconium and titanium; X4 is at least one element selected from phosphorus, tellurium, antimony, tin, cerium, lead, niobium, manganese, arsenic and zinc; and O is oxygen, and a, b, c, d, e, f, g and x are the atomic ratios of Mo, Bi, Fe, X1, X2, X3, X4 and O, respectively; when a=12, b=0.1-10, c=0.1-20, d=2-20, e=0.001-10, f=0-30, g=0-4, and x is a numerical value determined by the oxidation state of each of the other elements) can be named.

Also as the second stage catalyst, for example, oxidation catalysts represented by the following general formula (II):

$$Mo_h V_i W_j Y1_k Y2_l Y3_m Y4_n O_y \quad (II)$$

(wherein Mo is molybdenum; V is vanadium; W is tungsten; Y1 is at least one element selected from antimony, bismuth, chromium, niobium, phosphorus, lead, zinc and tin; Y2 is at least one element selected from copper and iron; Y3 is at least one element selected from alkali metals, alkaline earth metals and thallium; Y4 is at least one element selected from silicon, aluminum, titanium, zirconium, yttrium, rhodium and cerium; and O is oxygen; and h, i, j, k, l, m, n and y are the atomic ratios of Mo, V, W, Y1, Y2, Y3, Y4 and O, respectively; when h=12, i=2-14, j=0-12, k=0-5, l=0.01-6, m=0-5, n=0-10, and y is a numerical value determined by the oxidation state of each of the other elements)

The shape of those catalysts are not critical. They can be used in any known shapes such as spherical, columnar or ring-formed.

Each of the catalysts filled in the first reaction zone and the second reaction zone is not necessarily a single catalyst. For example, plural kinds of first stage catalysts of different activity levels may be used in the first reaction zone and arranged in the different order of their activity levels, or a part of the catalyst system may be diluted with inert carrier. Such variation in catalyst is applicable also to the second reaction zone.

The temperature suitable at the first reaction zone is normally 300-380° C., and that at the second reaction zone is normally 250-350° C. It is convenient that the difference in entering temperature and leaving temperature of the heat transfer medium both in the first reaction zone and in the second reaction zone is made not more than 10° C., preferably not more than 5° C. Incidentally, temperature of the first reaction zone and that in the second reaction zone as referred to in this invention substantially correspond to the respective entering temperature of the heat transfer medium into the reaction zones, and the entering temperatures of the heat transfer medium are determined according to the respectively prescribed temperatures at the first and second reaction zones, within the above-specified ranges.

Such temperature control at the reaction zones can be effected by separate circulations of a heat transfer medium whose temperature is respectively controlled by the heat transfer medium circulating devices externally mounted on the reactor, through the shell portions of the respective reaction zones. The circulating direction of the heat transfer medium is not critical. For example, in FIG. 3 the heat transfer medium is circulated upward from a lower part both in the first and second reaction zones, but the direction may be reversed, or it may be circulated downward from an upper part in the first reaction zone and upward from a lower part in the second reaction zone, or vice versa.

For regulating the flows of the heat transfer medium in each portion of the shell, preferably baffle plates such as those described in JP 2001-137689A can be mounted, which enhances elimination efficiency of the heat generated in the oxidation reaction by the heat transfer medium.

Furthermore, it is also possible to provide a partition plate or plates inside the shell of each reaction zone to divide it into two or more compartments and separately circulate a heat transfer medium therethrough, to separately control temperature of each compartment. In that case, the partition plates may be directly fixed on the reaction tubes by welding or like means. However, for preventing occurrence of thermal distortion in the partition plates or reaction tubes, it is recommendable to provide adequate apertures between the partition plates and reaction tubes, within an extent allowing the heat transfer medium circulations substantially independently of each other.

More specifically, the apertures or spaces between a partition plate and the reaction tubes are preferably made around 0.2-5 mm. The partition plates may be directly fixed on inner wall of the reactor by such means as welding, or may be fixed through a cylindrical mounting plate as described in JP Hei 7(1995)-73674B.

The gaseous substance to be added from outside the reactor into the space between the first reaction zone and second reaction zone is not particularly limited so long as it can achieve adjustment of the composition of the gas to one desired at the second reaction zone. For example, air, oxygen, nitrogen, steam, waste gas (recycled gas) and their gaseous mixture can be used.

Figure 5:
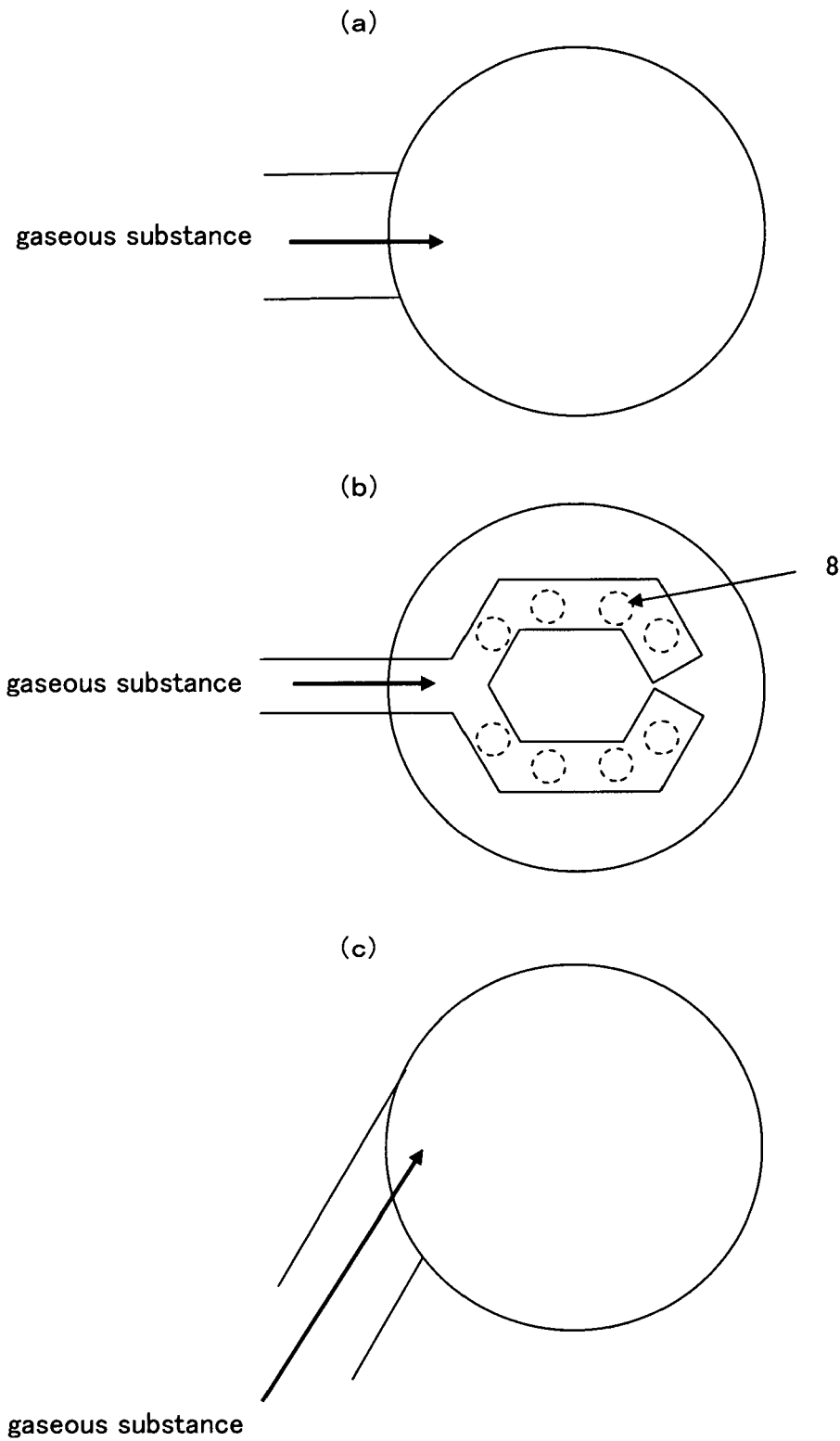
FIG. 5 shows, as schematic diagrams, cross-sections of various embodiments of introduction part of a gaseous substance to be added to the reactor in the reaction apparatus according to the present invention, in which (a) is a diagram showing cross-section of normal introduction part; (b) is that showing a case wherein a mechanism for increasing contact area by provision of many blowoff openings for the additional gaseous substance is provided; and (c) is that showing a case wherein a mechanism for creating a spiral flow by introducing the additional gaseous substance into the reactor at an oblique direction is provided.
Figure 6:
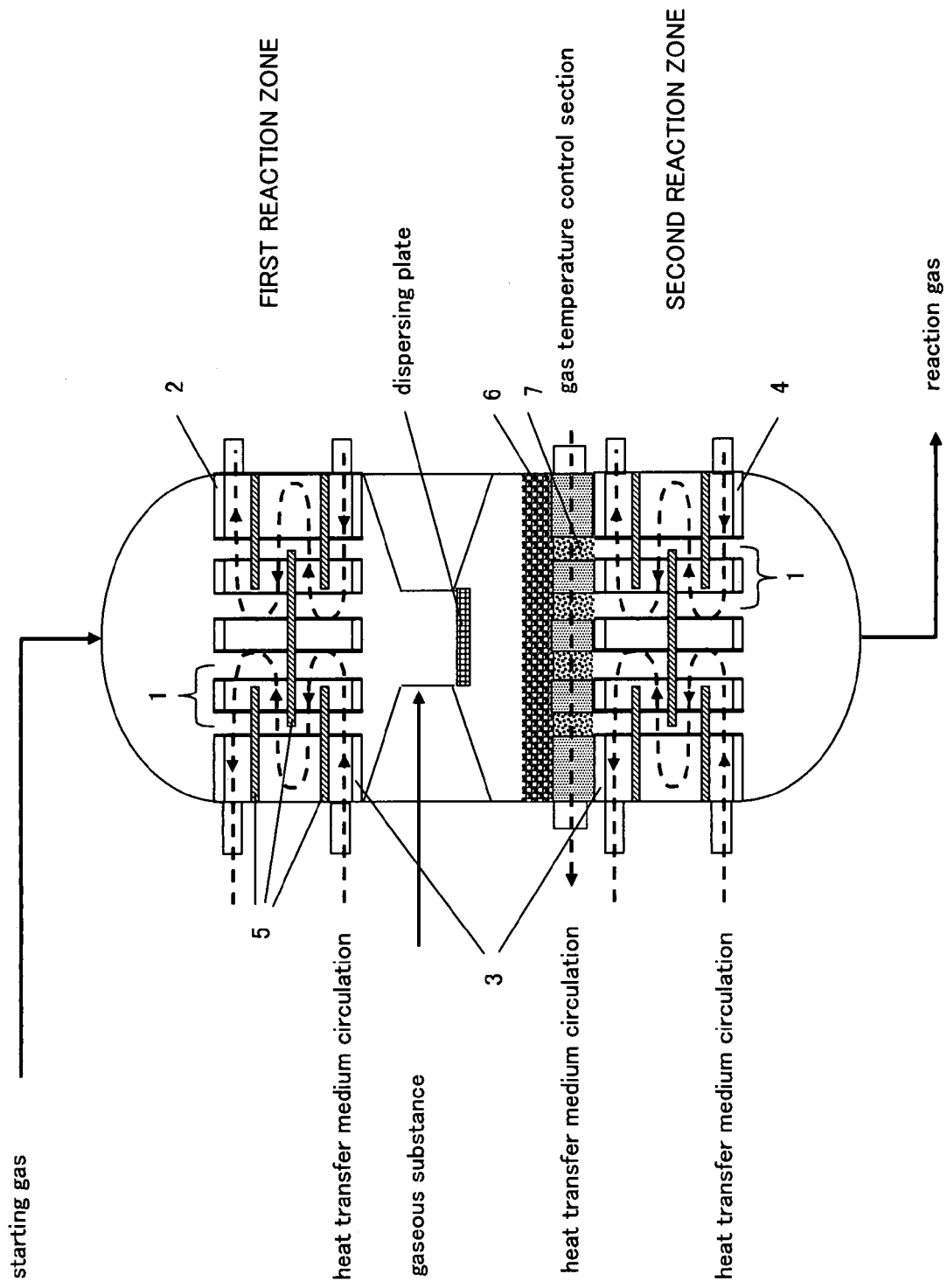
FIG. 6 is a schematic diagram of a reaction apparatus according to the present invention. In this embodiment, the space between the first reaction zone and the second reaction zone is given a constricted part and a dispersing plate is disposed under the constricted part, as a mechanism to efficiently mix the outlet gas from the first reaction zone with the added gaseous substance.

In the present invention, preferably a mechanism for efficiently mixing the outlet gas from the first reaction zone with the additional gaseous substance is provided in the space, which allows reduction in volume of the space and, in consequence, reduction in the reactor size. Such a mixing mechanism is not particularly limited and it may be, for example, the following:

(i) provision of many blowoff openings (8) for the additional gaseous substance to increase the contact area and mix the two (FIG. 5(*b*));

(ii) introduction of the additional gaseous substance at an oblique direction into the reactor, to effect the mixing with a spiral flow (FIG. 5(*c*)); for example, the gaseous substance can be introduced at horizontally oblique direction into the reactor; or (iii) introduction of the additional gaseous substance into a constricted part provided in the space between the first reaction zone and the second reaction zone, to effect the mixing by a dispersing plate disposed under the constriction.

Figure 4:
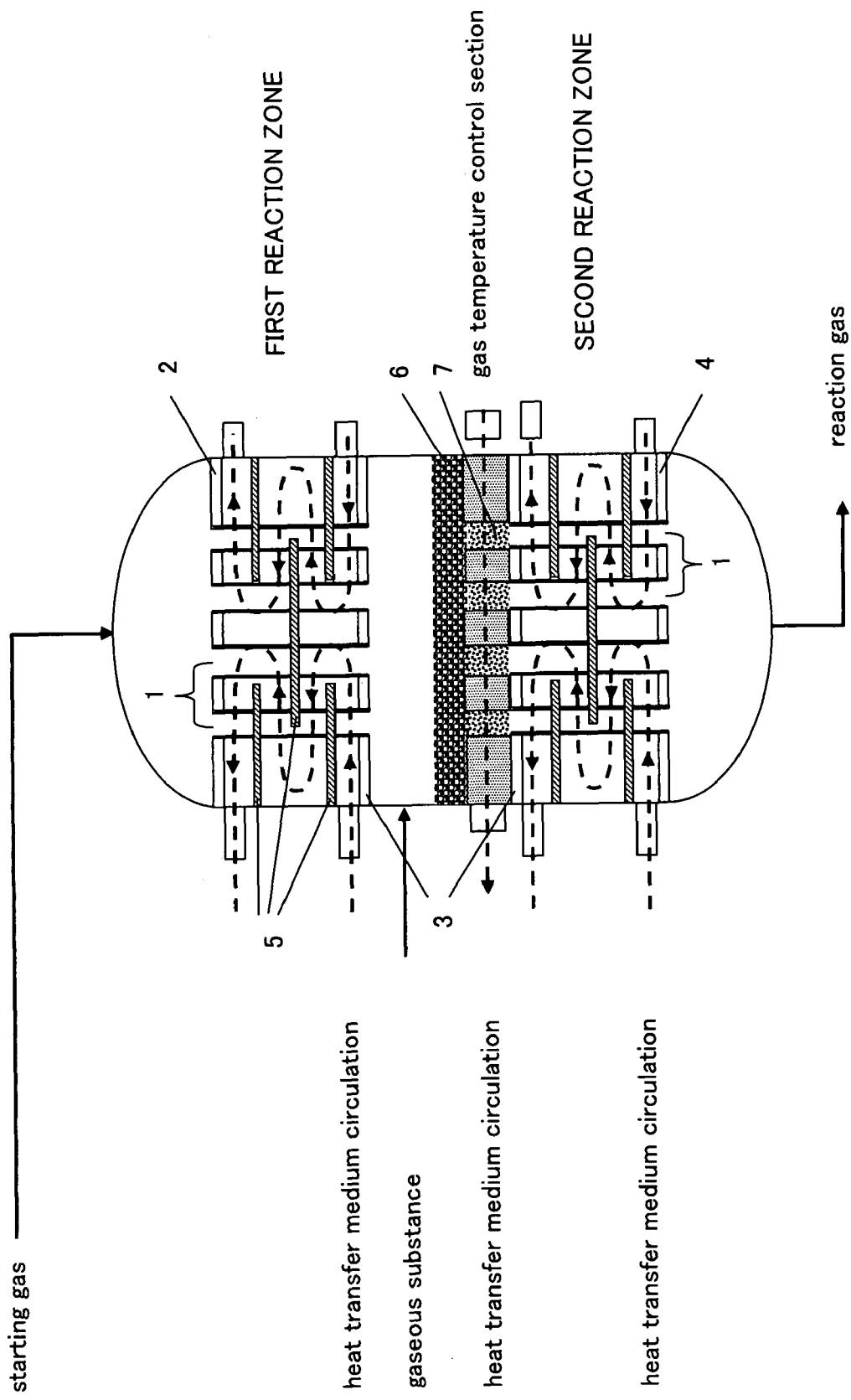
FIG. 4 is a schematic diagram of a reaction apparatus according to the present invention. In the embodiment of this diagram, the space provided in the reactor is filled with an inert substance, and a gas temperature control section filled with an inert substance is provided between the space and the second reaction zone.

According to the invention, moreover, a substance (6) which is substantially inert to the reaction gas may fill the space, as indicated in FIG. 4.

The kind of the substance substantially inert to the reaction gas is not critical. For example, it may be α-alumina, alundum, mullite, carborundum, stainless steel, silicon carbide, steatite, earthen ware, porcelain, iron and various ceramics and the like. The shape of such a substance also is not critical, so long as a significant rise in pressure loss is not caused by the inert substance itself. For example, it may be Raschig ring-formed, spherical, columnar or ring-formed grains, or may be in the form of bulk, bar, plate or net.

The outlet gas from the first reaction zone has relatively high temperature and the acrolein contained therein as the main component is apt to undergo a post-reaction such as autoxidation. Filling of an inert substance as above in the space shortens the residence time of the gas in the space, and is effective for preventing autoxidation of acrolein. Preferably, the filling amount of the inert substance is so selected as to render the residence time of the gas in the space no longer than 6 seconds.

Filling of such an inert substance is also effective to reduce contamination of the catalyst filled in the second reaction zone by molybdenum component scattered from the catalyst layer filled in the first reaction zone, high boiling point substance such as terephthalic acid formed in the first stage reaction as a by-product, or carbides accompanying autoxidation of acrolein. The reduction in contamination of the catalyst leads to prevention of deterioration in the catalytic performance, blockage of the space or rise in the pressure loss.

It is also preferred in the present invention to provide a gas temperature control section between the space and the second reaction zone as shown in FIG. 4, for cooling or heating the gaseous mixture of the outlet gas from the first reaction zone and the additional gaseous substance to a temperature within a range suitable for the reaction in the second reaction zone.

With this gas temperature control section, the outlet gas from the first reaction zone can be sufficiently cooled off within a short time and such a post-reaction as autoxidation of acrolein can be suppressed.

On the other hand, when the inlet gas into the second reaction zone is excessively cooled off by the gaseous substance supplied from outside, for example, sufficient catalytic activity cannot be obtained in the second reaction zone. The gas temperature control section can heat the gaseous mixture sufficiently to a temperature required for the second stage reaction within a short time.

The structure of the gas temperature control section is not critical. For example, a fin tube may be laid in the space in zigzag line, or plural tubes through which the reaction gas passes are disposed in the shell portion through which a heat transfer medium passes. The latter is the preferred, and in that occasion the reaction gas-passing tubes may contain no filling but are empty. Preferably, however, the reaction gas-passing tubes are filled with a substance (7) which is substantially inert to the reaction, as shown in FIG. 4, to facilitate heat-exchange between the heat transfer medium and the reaction gas.

The inert substance to be filled is subject to no particular limitation. Examples of useful substance are α-alumina, alundum, mullite, carborundum, stainless steel, silicon carbide, steatite, earthen ware, porcelain, iron and various ceramics. The shape of such a substance is not also critical, so long as a significant rise in pressure loss is not caused by the inert substance itself. For example, it may be Raschig ring-formed, spherical, columnar or ring-formed grains, or may be in the form of bulk, bar, plate or net.

The temperature control at the gas temperature control section may also be effected by circulating a heat transfer medium therethrough independently of each of the reaction zones, or by circulating the same heat transfer medium for the first reaction zone or that for the second reaction zone.

When the gas temperature control section is used for cooling the outlet gas from the first reaction zone and/or as preheating layer for controlling the temperature of the reaction gas in the second reaction zone, the temperature of the gas temperature control section can be controlled by independently circulating a heat transfer medium therethrough, or by circulating the heat transfer medium which is going to enter the second reaction zone or that leaving the second reaction zone therethrough.

The shortening of residence time of the gas in the space or adjustment of the gas concentration by introduction of additional gas according to the present invention achieve remarkable improvement in preventing formation of carbides generated from autoxidation of acrolein or caused by such high boiling point substances as terephthalic acid, compared with conventional methods of producing acrylic acid by oxidation of propylene over a long term under high load conditions. In the long-term production, however, when the outlet gas from the first reaction zone is cooled, not a little carbides are formed on the catalyst at the entrance of the second reaction zone or, when the space or the gas temperature control section are filled with an inert substance, on the filled inert substance, which can be a cause for blockage or rise in pressure loss.

The troubles caused by the carbides formed on the catalyst at the entrance of the second reaction zone or on the inert substance can be overcome, by regularly exchanging the catalyst at the entrance of the second reaction zone or the inert substance, preferably at a frequency of at least once a year, or by eliminating the carbides by combustion, by means of aeration passing an oxygen-containing gas under high temperature.

In practicing such an aeration, normally the second stage catalyst develops deterioration in its catalytic performance, due to the contact with the oxygen-containing gas at high temperatures. The second reaction zone, therefore, should be kept at no higher than 350° C., preferably no higher than 330° C., inter alia, no higher than 320° C. That is, only the first reaction zone and/or gas temperature control section are kept at a temperature of 320° C. or higher. In actual operation, it is also possible to independently circulate another heat transfer medium, or the same heat transfer medium having a relatively high temperature before its introduction into, or after its departure from, the first reaction zone, through the gas temperature control section.

EXAMPLES

Hereinafter the present invention is explained more specifically, referring to working Examples, it being understood that the invention is in no way thereby limited. In the following, "mass parts" may be simply indicated as "parts", for expediency.

Example 1

[Preparation of the First Stage Catalyst 1]

In 300 parts of distilled water, 192.6 parts of ammonium molybdate and 42.2 parts of ammonium paratungstate were dissolved under heating and stirring. Into this solution a liquid mixture of three nitrate solutions obtained respectively by dissolving 79.4 parts of cobalt nitrate in 30 parts of distilled water, 40.4 parts of ferric nitrate in 40 parts of distilled water, and 52.9 parts of bismuth nitrate in 60 parts of nitric acid which had been made of distilled water and 10 volume parts of concentrated nitric acid, was dropped. Successively, 0.234 part of potassium hydroxide as dissolved in 15 parts of distilled water was added. The resultant suspension was heated under stirring and evaporated. The residue was molded and calcined for 8 hours at 460° C. under air flow, to provide a catalyst. The metallic composition of this catalyst was as follows, in terms of atomic ratio:

$Mo_{12}Bi_{1.2}Fe_{1.1}Co_3K_{0.05}W_2$.

[Preparation of the Second Stage Catalyst 1]

Into 2000 parts of distilled water, 365.4 parts of ammonium paramolybdate, 113 parts of ammonium metavanadate and 46.6 parts of ammonium paratungstate were dissolved under heating and stirring. Separately, 95.8 parts of copper nitrate was dissolved in 400 parts of distilled water under heating and stirring. Thus obtained two solutions were mixed and poured in a porcelain evaporator on a hot water bath, and into which 1000 volume parts of spherical carrier of 3-5 mm in diameter, made of α-alumina was added. The system was evaporated under stirring and dried to solid which deposited on the carrier. Upon calcining the same at 400° C. in the atmosphere of air for 6 hours, a catalyst was obtained, which had the following metallic composition in terms of atomic ratio:

$Mo_{12}V_5W_{1.2}Cu_2$.

[Reactor and Oxidation Reaction]

A reactor of 400 mm in inner diameter, which accommodates, in the order from the top, the first reaction zone (24 SUS reaction tubes each 3,000 mm in length and 25 mm in inner diameter), a space (1000 mm in length; a gas introduction pipe was disposed in a tangential direction to the reactor at 800 mm above a gas temperature control section), a gas temperature control section (24 pipes of each 500 mm in length and 25 mm in inner diameter) and the second reaction zone (24 SUS reaction tubes of each 3,000 mm in length and 25 mm in diameter), was used (cf. FIG. 4).

The first reaction zone was filled with the first stage catalyst 1 to a length of 3000 mm, and the second reaction zone was filled with the second stage catalyst 1 to a length of 3000 mm.

The space was filled with, as an inert substance, ceramic balls of each 40 mm in diameter in such a manner that the residence time of the gas in the space should be 6 seconds.

The gas temperature control section was filled with, as an inert substance, SUS Raschig rings of each 6 mm in outer diameter and 7 mm in length, to a length of 500 mm. A heat transfer medium was flown upward from a lower part, in all of the first reaction zone, gas temperature control section and the second reaction zone, respectively. A starting gas having the following composition was introduced from above the reactor, and the oxidation was conducted under the conditions given below.
<Composition of Starting Gas>
propylene, 6 vol. %; oxygen 8 vol. %; steam, 7 vol. % and inert gas such as nitrogen, 79 vol. %.
<Gas Flow Rate>
The gas having above composition was supplied at a rate of 47.7 m³/Hr.
<Additional Gas>
Air was supplied into the space at a rate of 13.6 m³/Hr.
<Temperature at the Catalyst Layers>
First reaction zone temperature (entrance temperature of heat transfer medium into the first reaction zone): 320° C.
Second reaction zone temperature: entrance temperature of heat transfer medium into the second reaction zone): 265° C.
<Temperature at the Gas Temperature Control Section>
Entrance temperature of heat transfer medium into gas temperature control section: 265° C.
Propylene conversion and acrylic acid yield at 24 hours and 4,000 hours after initiation of the reaction were, respectively:
after 24 hours; propylene conversion, 98.4 mol % acrylic acid yield, 90.0 mol %
after 4,000 hours; propylene conversion, 98.1 mol % acrylic acid yield, 90.2 mol %.

Example 2

[Preparation of First Stage Catalyst 2]

Into 1,000 parts of distilled water, 385.2 parts of ammonium molybdate and 39.3 parts of ammonium paratungstate were dissolved under heating and stirring (solution A). Separately, 264.6 parts of cobalt nitrate was dissolved in 140 parts of distilled water (solution B); 80.8 parts of ferric nitrate, in 80 parts of distilled water (solution C); and 105.8 parts of bismuth nitrate was dissolved in 100 parts of nitric acid which had been made of 100 volume parts of distilled water and 20 volume parts of nitric acid (60%) (solution D). These three kinds of nitrate solutions (solutions B, C and D) were dropped into the solution A. Successively, 0.469 part of potassium hydroxide as dissolved in 30 parts of distilled water was added. Thus obtained suspension was heated, stirred and evaporated, molded into a size of each 8 mm in outer diameter, 3 mm in inner diameter and 7 mm in length, and calcined at 460° C. for 8 hours under an air flow to provide a catalyst. The metallic composition of this catalyst excluding oxygen was as follows, in terms of atomic ratio:

$Mo_{12}Bi_{1.2}Fe_{1.1}Co_{5.0}K_{0.05}W_{0.8}$.

[Preparation of First Stage Catalyst 3]

The catalyst 3 was prepared in the same manner as in the first stage catalyst 2, except that the size of the molded catalyst was 6 mm in outer diameter, 2 mm in inner diameter and 6 mm in length.

[Preparation of Second Stage Catalyst 2]

Into 2,000 parts of distilled water, 365.4 parts of ammonium paramolybdate, 100.9 parts of ammonium metavanadate and 55.9 parts of ammonium paratungstate were dissolved under heating and stirring. Separately, 83.3 parts of copper nitrate was dissolved in 400 parts of distilled water under heating and stirring. The two solutions were mixed and poured in a porcelain evaporator on a hot water bath, and into the evaporator 1,000 volume parts of spherical carrier made of α-alumina, having an average particle diameter of 8 mm was added. The system was evaporated to dryness under stirring to deposit the catalyst component on the carrier, followed by calcination at 400° C. for 6 hours in an atmosphere of air, to provide a catalyst. The metallic composition of this catalyst excluding oxygen was as follows, in terms of atomic ratio:

$Mo_{12}V_5W_{1.2}Cu_2$.

[Preparation of Second Stage Catalyst 3]

The catalyst was prepared in the same manner to the second stage catalyst 2, except that spherical carrier of 5 mm in average particle diameter was used.

[Reactor and Oxidation Reaction]

A reactor of 400 mm in inner diameter accommodating, in the order from the top, the first reaction zone (24 SUS reaction tubes each 3000 mm in length and 25 mm in inner diameter), a space (1500 mm in length; a gas inlet pipe was disposed at a perpendicular direction to the reactor at 1300 mm above the upper tube plate of the second reaction zone) and the second reaction zone (24 SUS reaction tubes of each 3,000 mm in length and 25 mm in inner diameter) was used (cf. FIG. 3 and FIG. 5 (a)).

The first reaction zone was filled with, from the gas inlet side, first stage catalyst 2 to a length of 800 mm, first stage catalyst 3 to a length of 2200 mm; and the second reaction zone was filled with, from the gas inlet side, second stage catalyst 2 to a length of 700 mm and second stage catalyst 3 to a length of 2300 mm.

A heat transfer medium was flown upward from a lower part, in both the first reaction zone and the second reaction zone. A starting gas having the following composition was introduced from above the reactor, and the oxidation was operated under the conditions given below.
<Composition of Starting Gas>
propylene, 12 vol. %; oxygen, 15 vol. %; steam, 9 vol. % and inert gas such as nitrogen, 64 vol. %.
<Gas Flow Rate>
The gas having above composition was supplied at a rate of 47.7 m³/Hr.
<Additional Gas>
Air was supplied into the space at a rate of 13.6 m³/IHr.
<Temperature at the Catalyst Layers>
First reaction zone temperature (entrance temperature of heat transfer medium into the first reaction zone): 320° C.
Second reaction zone temperature (entrance temperature of heat transfer medium into the second reaction zone): 265° C.
<Performance Evaluation>
Propylene conversion and acrylic acid yield at 48 hours and 4000 hours after initiation of the reaction, and rise in pressure loss after 4000 hours' operation from the initiation time were as shown in Table 1.

When condition of the reactor after 4000 hours' operation was examined, deposition of carbides was observed on the catalyst layers over a length of 30 mm from the entrance of the second reaction zone.
<Aeration>
A gaseous mixture composed of oxygen, 12 vol. %; steam, 50 vol. % and inert gas such as nitrogen, 38 vol. %; was passed through the reactor for 24 hours at a flow rate of 21.2 m³/Hr, while maintaining the temperature of 350° C. in the first reaction zone and that of 320° C. in the second reaction zone. As the result of this aeration, removal of the carbides without rapid rise in the catalyst layer temperature was confirmed, and the elevated pressure loss returned to the level at the incipient period of the reaction. The performance evaluation after that treatment is also shown in Table 1.

Example 3

The reaction was operated under the same conditions as Example 2, except that the additional gas inlet pipe was disposed at a tangential direction to the reactor (cf. FIGS. 3 and 5(*c*)). The result was as shown in Table 1.

When condition of the reactor after 4000 hours' operation was examined, deposition of carbides was observed on the catalyst layers over a length of 10 mm from the entrance of the second reaction zone. Thereafter an aeration was carried out under the same conditions as Example 2, and after that removal of the carbides without rapid rise in temperature at the catalyst layer was confirmed. The pressure loss also returned to the level at the incipient period of the reaction. The performance evaluation after that treatment is also shown in Table 1.

Example 4

[Reactor and Oxidation Reaction]

A reactor of 400 mm in inner diameter, which accommodates, in the order from the top, the first reaction zone (24 SUS reaction tubes each 3000 mm in length and 25 mm in inner diameter), a space (1,500 mm in length; a gas inlet pipe was disposed in a tangential direction to the reactor at 1,300 mm above a gas temperature control section), a gas temperature control section (24 pipes of each 500 mm in length and 25 mm in inner diameter) and the second reaction zone (24 SUS reaction tubes of each 3,000 mm in length and 25 mm in diameter), was used.

The first reaction zone was filled with, from the gas inlet side, first stage catalyst 2 to a length of 700 mm and first stage catalyst 3 to a length of 2300 mm; and the second reaction zone was filled with, from the gas inlet side, second stage catalyst 2 to a length of 800 mm and second stage catalyst 3 to a length of 2200 mm.

The gas temperature control section was filled with, as an inert substance, SUS Raschig rings of each 6 mm in outer diameter and 7 mm in length, to a length of 500 mm. A heat transfer medium was flown upward from a lower part, in both the first reaction zone and the second reaction zone, respectively. The heat transfer medium temperature at the entrance of the gas temperature control section was kept at 260° C. The reaction conditions were the same as those of Example 2. The results were as shown in Table 1.

Condition of the reactor after 4000 hours' operation was examined. Although deposition of carbides was observed on the inert substance filled in the gas temperature control section, none was on the catalyst layer. Whereupon an aeration was conducted under the same conditions as in Example 2, except that the temperature of the heat transfer medium at the gas temperature control section was raised to 340° C. Removal of the carbides without rapid rise in temperature at the catalyst layer was confirmed. The pressure loss also returned to the level at the incipient period of the reaction. The performance evaluation after that treatment is also shown in Table 1.

Example 5

The reaction was operated under the same conditions as those of Example 4, except that the space was filled with, as an inert substance, ceramic balls of 40 mm in diameter in such a manner that the residence time of the gas in the space should be 6 seconds (cf. FIGS. 4 and 5(*c*)). The result was as shown in Table 1.

Condition of the reactor was examined after 4,000 hours' operation. Deposition of a little carbides was observed on the surface of the inert substance filling the space, but no carbides was observed on the inert substance filling the gas temperature control section and the catalyst layer. Thereafter an aeration was conducted under the same conditions as those in Example 2. Removal of the carbides without rapid rise in temperature at the catalyst layer was confirmed. The pressure loss also returned to the level at the incipient period of the reaction. The performance evaluation after that treatment is also shown in Table 1.

Comparative Example 1

The reaction was operated using a conventional two reactor-type reaction apparatus and the catalysts same to those in Example 2.

[Reactor and Oxidation Reaction]

Figure 1:
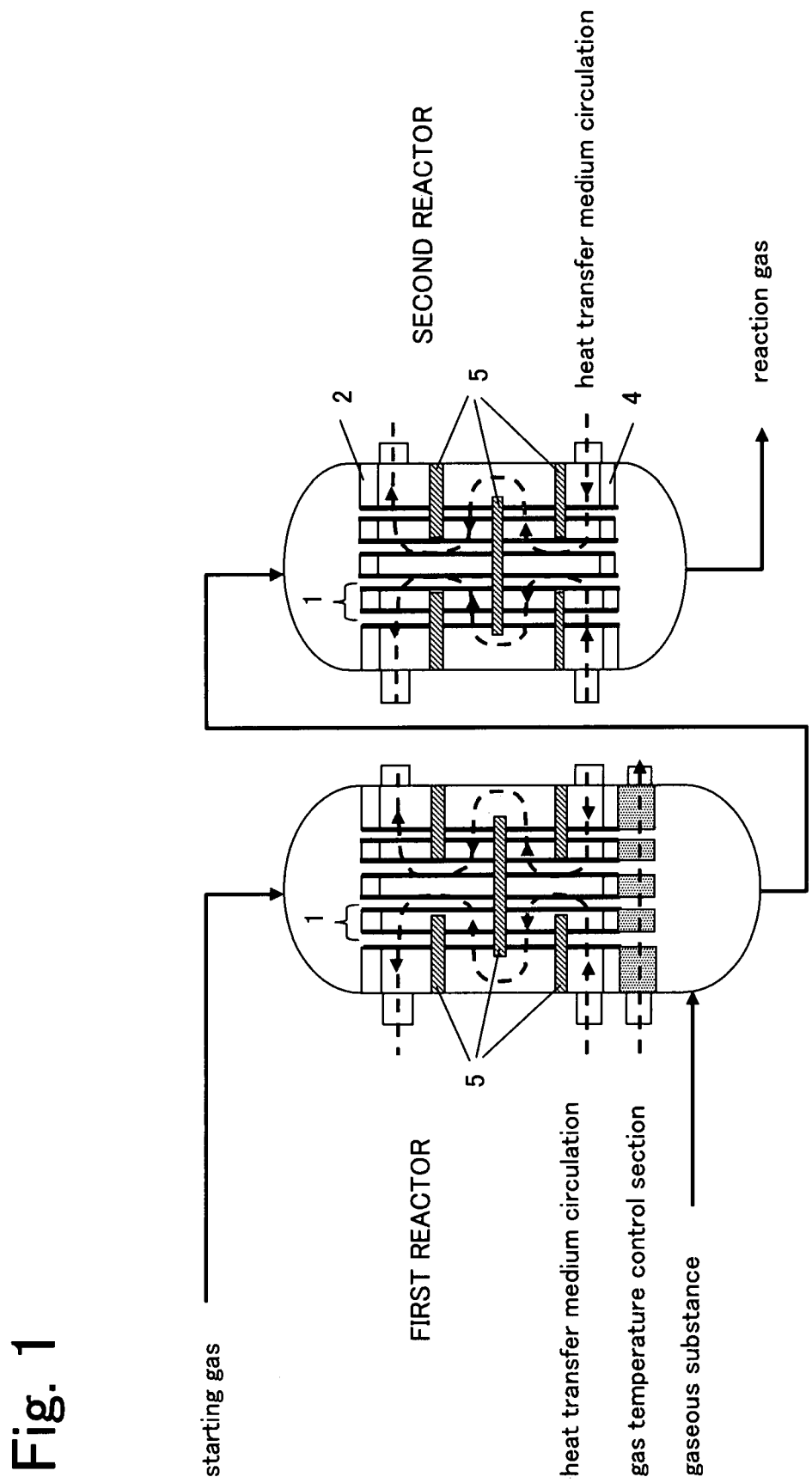
FIG. 1 is a schematic diagram of a conventional reaction apparatus comprising two reactors.
Figure 2:
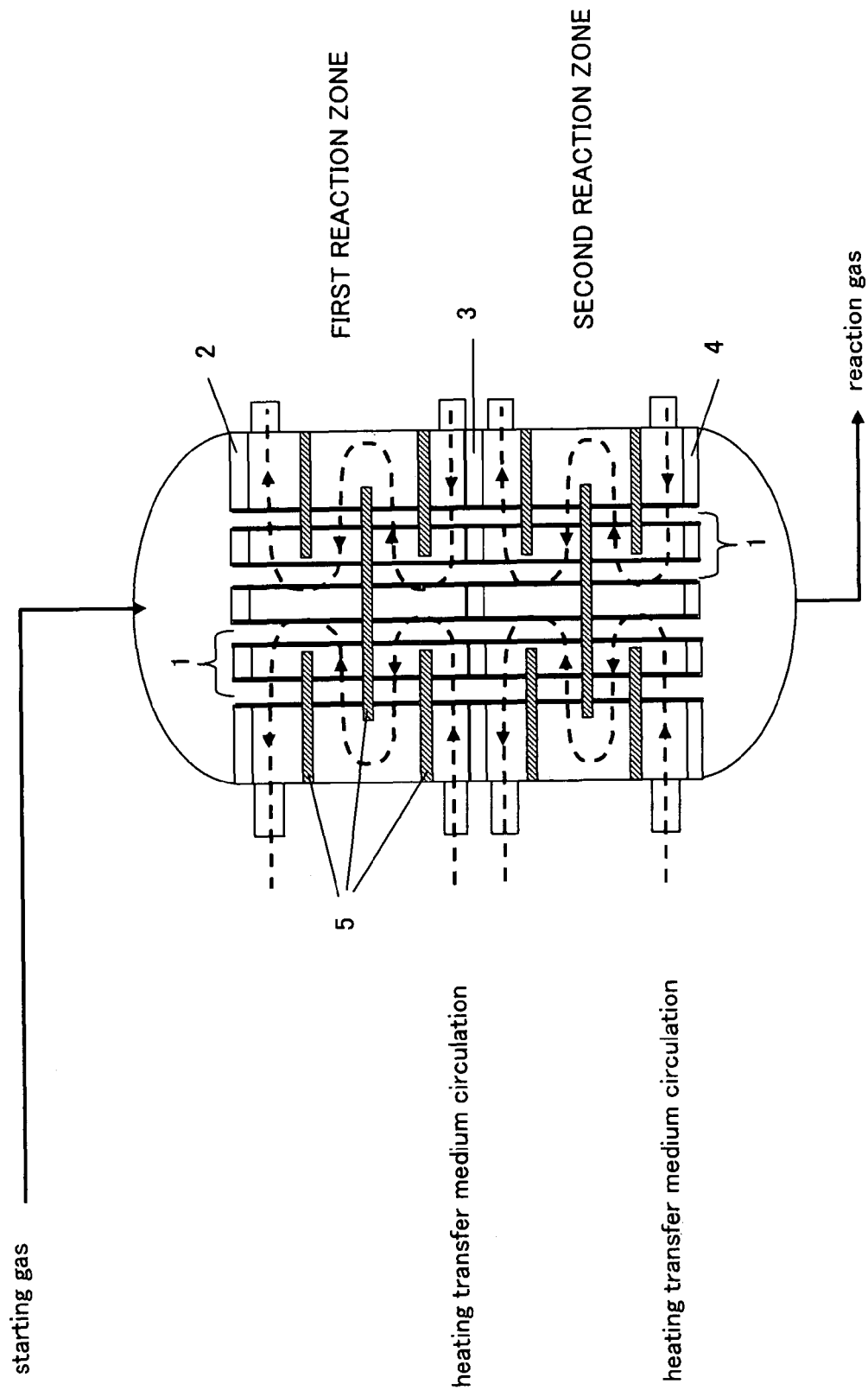
FIG. 2 is a schematic diagram of a conventional reaction apparatus comprising a single reactor.

A reaction apparatus of 400 mm in inner diameter was used, which was composed of a first reactor (24 SUS reaction tubes of each 3000 mm in length and 25 mm in inner diameter), a gas temperature control section at the exit of the first reactor (24 pipes of each 500 mm in length and 25 mm in inner diameter) and a second reactor (24 SUS reaction tubes of each 3000 mm in length and 25 mm in inner diameter). The reactors were connected with a SUS pipe of 200 mm in inner diameter and 6000 mm in length. Furthermore, at the exit of the first reaction zone a pipe for additional gas introduction was provided (cf. FIG. 1).

The first reactor was filled with, from its gas inlet side, first stage catalyst 2 to a length of 800 mm and first stage catalyst 3 to a length of 2200 mm; and the second reactor was filled with, from its gas inlet side, second stage catalyst 2 to a length of 700 mm and second stage catalyst 3 to a length of 2300 mm.

The gas temperature control section at the exit of the first reaction zone was filled with SUS Raschig rings of each 6 mm in outer diameter and 7 mm in length, to a length of 500 mm. The heat transfer medium was flown upward from a lower part in both the first and second reaction zones, respectively, and a starting gas having the following composition was introduced from above the reaction apparatus to be subjected to an oxidation reaction under the following conditions:

<Composition of Starting Gas> propylene, 12 vol. %; oxygen, 15 vol. %; steam, 9 vol. % and inert gas such as nitrogen, 64 vol. %<

<Flow Rate>

The gas of the above composition was supplied at a rate of 47.7 m³/Hr.

<Additional Gas>

Air was supplied at a rate of 13.6 m²/Hr.

<Temperatures at the Catalyst Layers>

First reaction zone temperature (entrance temperature of heat transfer medium into the first reaction zone): 320° C.

Gas temperature control section temperature (entrance temperature of heat transfer medium into the gas temperature control section): 260° C.

Second reaction zone temperature (entrance temperature of heat transfer medium into the second reaction zone): 265° C. The result was as shown in Table 1.

Condition of the reactor after 4000 hours' operation was examined. Deposition of carbides on the reactor-connecting pipe and the inert substance was observed, and furthermore carbides were found on the catalyst over a distance of 200 mm from the entrance of the second reaction zone.

<Aeration>

A gaseous mixture composed of oxygen, 12 vol. %; steam, 50 vol. % and inert gas such as nitrogen, 38 vol. %; was passed through the reactors for 24 hours at a flow rate of 21.2 m³/Hr, while maintaining the temperature of 350° C. in the first reaction zone and that of 320° C. in the second reaction zone.

However, this aeration was discontinued midway because of rapid rise (run-away) in the catalyst layer temperature. Thereafter the reaction was resumed but the catalyst had been deactivated, rendering continuation of the reaction impossible.

TABLE 1

| | Time | Propylene conversion (mol %) | Acrylic acid yield (mol %) | Rise in pressure loss (kPa) |
|---|---|---|---|---|
| Example 2 | After 48 hours | 97.8 | 87.6 | 0.93 |
| | After 4000 hours | 96.2 | 86.1 | |
| | After aeration | 97.8 | 87.7 | initial level |
| Example 3 | After 48 hours | 98.2 | 88.1 | 0.89 |
| | After 4000 hours | 96.6 | 86.7 | |
| | After aeration | 98.1 | 88.1 | initial level |
| Example 4 | After 48 hours | 98.2 | 88.4 | 0.71 |
| | After 4000 hours | 97.8 | 87.9 | |
| | After aeration | 98.1 | 88.3 | initial level |
| Example 5 | After 48 hours | 98.4 | 90.0 | 0.35 |
| | After 4000 hours | 98.1 | 90.2 | |
| | After aeration | 98.4 | 90.1 | initial level |
| Comparative Example 1 | After 48 hours | 98.1 | 87.5 | 5.5 |
| | After 4000 hours | 94.1 | 82.9 | |
| | After aeration | Not measured because of deactivation | | |

The invention claimed is:

1. A process for producing acrylic acid by a two-stage gas-phase catalytic oxidation of propylene, comprising:
reacting a reaction gas comprising propylene using a fixed bed shell-and-tube reaction apparatus that comprises a single reactor which is used for gas-phase catalytic oxidation reaction, wherein the reactor has an interior which is divided into two reaction zones, a first reaction zone and a second reaction zone, and has a space equipped with a mechanism for introducing a gaseous substance from outside the reactor provided between the two reaction zones, and wherein the space in the reactor is equipped with a mechanism for mixing an outlet gas from the first reaction zone with an additional gaseous substance.

2. The process according to claim 1 in which the space in the reactor is filled with a substance which is inert to the reaction gas.

3. The process according to claim 1, in which oxide catalysts represented by the following general formula (I):

$$Mo_aBi_bFe_cX1_dX2_eX3_fX4_gO_x \qquad (I),$$

wherein Mo is molybdenum; Bi is bismuth; Fe is iron; X1 is at least one element selected from cobalt and nickel; X2 is at least one element selected from alkali metals, alkaline earth metals and thallium; X3 is at least one element selected from tungsten, silicon, aluminum, zirconium and titanium; X4 is at least one element selected from phosphorus, tellurium, antimony, tin, cerium, lead, niobium, manganese, arsenic and zinc; and O is oxygen, and a, b, c, d, e, f, g and x are the atomic ratios of Mo, Bi, Fe, X1, X2, X3, X4 and O, respectively; when a=12, b=0.1-10, c=0.1-20, d=2-20, e=0.001-10, f=0-30, g=0-4, and x is a numerical value determined by the oxidation state of each of the other elements, are filled in the first reaction zone, and oxidation catalysts represented by the following general formula (II):

$$Mo_hV_iW_jY1_kY2_lY3_mY4_nO_y \qquad (II),$$

wherein Mo is molybdenum; V is vanadium; W is tungsten; Y1 is at least one element selected from antimony, bismuth, chromium, niobium, phosphorus, lead, zinc and tin; Y2 is at least one element selected from copper and iron; Y3 is at least one element selected from alkali metals, alkaline earth metals and thallium; Y4 is at least one element selected from silicon, aluminum, titanium, zirconium, yttrium, rhodium and cerium; and O is oxygen; and h, i, j, k, l, m, n and y are the atomic ratios of Mo, V, W, Y1, Y2, Y3, Y4 and O, respectively; when h =12, i=2-14, j=0-12, k=0-5, l=0.01-6, m=0-5, n=0-10, and y is a numerical value determined by the oxidation state of each of the other elements, are filled in the second reaction zone.

4. The process according to claim 2, in which the inert substance is at least one of α-alumina, alundum, mullite, carborundum, stainless steel, silicon carbide, steatite, earthen ware, porcelain, iron and ceramic.

5. The process according to claim 1, in which a gas temperature control section is provided between the second reaction zone and the space.

6. The process according to claim 2, in which aeration is practiced at least once a year.

7. The process according to claim 6, in which aeration is practiced in the first reaction zone at a temperature of 320° C. or higher.

8. The process according to claim 6, in which aeration is practiced in the second reaction zone at a temperature of no higher than 350° C.

9. The process according to claim 7, in which aeration is practiced also in the second reaction zone at a temperature of no higher than 350° C.

* * * * *